United States Patent
Paufique

(10) Patent No.: US 10,561,600 B2
(45) Date of Patent: Feb. 18, 2020

(54) COSMETIC ACTIVE INGREDIENT FOR COMBATING THE LOSS OF VOLUME OF TISSUES, IN PARTICULAR OF THE FACE

(71) Applicant: Jean Paufique, Objat (FR)

(72) Inventor: Jean Paufique, Objat (FR)

(73) Assignee: SOCIETE INDUSTRIELLE LIMOUSINE D'APPLICATION BIOLOGIQUE, Objat (FR)

(*) Notice: Subject to any disclaimer, the term of this patent is extended or adjusted under 35 U.S.C. 154(b) by 452 days.

(21) Appl. No.: 14/492,344

(22) Filed: Sep. 22, 2014

(65) Prior Publication Data

US 2015/0086661 A1 Mar. 26, 2015

(30) Foreign Application Priority Data

Sep. 23, 2013 (FR) ...................................... 13 59109

(51) Int. Cl.
*A61K 36/65* (2006.01)
*A61K 8/97* (2017.01)
*A61Q 19/08* (2006.01)
*A61K 8/60* (2006.01)

(52) U.S. Cl.
CPC .................. *A61K 8/97* (2013.01); *A61K 8/60* (2013.01); *A61Q 19/08* (2013.01)

(58) Field of Classification Search
None
See application file for complete search history.

(56) References Cited

U.S. PATENT DOCUMENTS

2005/0265944 A1* 12/2005 Cowden .................. A61K 8/02
424/70.13
2008/0095731 A1* 4/2008 Mitra ...................... A61K 8/60
424/70.13

FOREIGN PATENT DOCUMENTS

JP 2000007550 A * 1/2000

OTHER PUBLICATIONS

Raskin et al. (2004) Current Pharmaceutical Design, 10, 3419-3429.*
Hansel, Rudolf, "Paeonia ED", Hagers Handbuch Der Pharmazeutischen Praxis, Drogen P=Z, 1994, pp. 1-12, XP009129693.
Wang et al., "Simultaneous LC Determination of Major Constituents in Red and White Peony Root", Chromatographia, 2005, vol. 62, pp. 581-588.
French Search Report, dated Apr. 30, 2014, from corresponding FR application.

* cited by examiner

*Primary Examiner* — Russell G Fiebig
(74) *Attorney, Agent, or Firm* — Young & Thompson

(57) ABSTRACT

A cosmetic active ingredient obtained from roots of *Paeonia albiflora*, which is a hydrolyzate of roots of *Paeonia albiflora* including at least 30% of carbohydrates by weight relative to the total weight of dry materials. The cosmetic active ingredient can be used in a composition and in a cosmetic care process for care of the human skin.

12 Claims, No Drawings

COSMETIC ACTIVE INGREDIENT FOR COMBATING THE LOSS OF VOLUME OF TISSUES, IN PARTICULAR OF THE FACE

FIELD OF THE INVENTION

This invention relates to an active ingredient that is intended to combat the loss of volume of tissues, in particular in the face. The object of this invention is also a use of this cosmetic active ingredient for a topical application of the skin. The invention also covers a cosmetic skin-care process.

BACKGROUND OF THE INVENTION

The phenomenon of ageing of the skin is linked to numerous factors and in particular relating to the face; with advancing age, a loss of volume at the cheeks, cheekbones, and temples is noted. This characteristic is very visible and deeply marks the face, which is, it must be recalled, the part of the human being that is always visible.

During this loss of volume, related effects unfortunately reinforce this impression; in particular, the lines become hollow, the contours sag, and wrinkles are accentuated.

The mechanism is complex. The shapes and the contours of the face result from deep subcutaneous structures that ensure the support thereof.

With age, muscle tone decreases, and the subcutaneous fatty mass moves toward the bottom of the face.

Ptosis appears and leads to the formation of jowls, in particular.

This phenomenon is not linear and is manifested more intensely on skin exposed to light.

The skin that is subjected to ultraviolet (UV) radiation becomes loose, wrinkled, rough and sprinkled with hypo-pigmented or hyper-pigmented spots.

The face, as indicated above, is always exposed, and 80% of its ageing is attributed to exposure to the sun.

Actually, the UV radiation, in addition to well-known structural changes of the epidermis and the dermis that it produces, causes an alteration in the functionality of the adipocytes. Their adipogenesis and lipogenesis capacities are diminished and the volumes of the adipocytes decrease, which produces a gradual melting of the subcutaneous fat.

In addition, the UV radiation, in particular the UVA, reaches the dermis but can also impact the hypodermis, while it is not reached by said radiation, in so doing by indirect actions.

SUMMARY OF THE INVENTION

Under the effect of UV radiation, the keratinocytes and the fibroblasts secrete soluble factors that cause deleterious effects in the hypodermis.

These soluble factors are inflammatory secretomes composed of different mediators including cytokines, growth factors and proteases that, by a paracrine action, modify the metabolic activities of the adipocytes, bringing about the loss of adipose tissue and its redistribution.

Facing this problem, it is appropriate to control the communication between the dermis and the hypodermis, in particular to act on the reduction of released pro-inflammatory cytokines to combat the effects of age and actions of UV radiation.

To ensure this control of the communication, this invention proposes resorting to a plant, more particularly the root of this plant, namely the root of the peony *Paeonia albiflora*.

The active ingredient according to this invention has as its object to preserve the functionality of the adipocytes.

DETAILED DESCRIPTION OF THE INVENTION

This invention is now described in detail, with the support of the test results.

Active Ingredient

The active ingredient according to this invention is obtained from the following process:
  Solubilization of powder from *Paeonia albiflora* roots in water,
  Enzymatic hydrolysis,
  Separation of soluble and insoluble phases,
  Enzymatic deactivation by heat treatment of the soluble fraction,
  Successive filtrations so as to select the oligosaccharides of sucrose and glucose, and
  Sterilizing filtration.

More particularly, the process consists of the series of the following steps:
  Solubilization of powder from *Paeonia albiflora* roots in water, at a rate of 50 g per liter,
  Enzymatic hydrolysis,
  Separation of soluble and insoluble phases,
  Thermal deactivation at 80° C. of the soluble fraction,
  Successive filtrations so as to eliminate the molecules of a size larger than 1,000 Daltons, and
  Sterilizing filtration on a membrane with a threshold of 0.22 µm.

The active ingredient thus obtained is a clear liquid with a clear yellow color. The characteristics of the active ingredient thus obtained are as follows:

Dry Material Level:

The level of dry material is obtained by weighing 3 ml of liquid of a clear yellow color thus obtained, added to 10 g of sand placed in an oven at 105° C. for 7 hours.

The level of dry material is from 20 to 90 g/l, preferably from 32 to 48 g/l.

Measurement of the pH:

The pH that is measured by the potentiometric method is preferably between 3.0 and 4.0.

Determination of the Total Sugar Content:

The total sugars are metered by the Dubois method [Dubois, M. et al. (1956), Analytical Chemistry, 28, 3, 350-356].

In the presence of concentrated sulfuric acid, the reducing sugars provide a yellow-orange-colored compound.

Two samples are thus compared:
  400 µl of active ingredient+400 µl (5%) of phenol+2,000 µl (95%) of sulfuric acid
  400 µl of water+400 µl (5%) of phenol+2,000 µl (95%) of sulfuric acid The composition, whose heating is linked to the exothermic reaction, is cooled. Next, the optical densities of the samples, measured with a spectrophotometer at the wavelength of 490 nm, are compared.

The same experiment is conducted on a standard range of glucose ranging from 25 to 125 µg/ml.

The level of total sugars of the active ingredient obtained with the spectrophotometer on the standard curve then just has to be read directly.

The quantity of total sugars is between 11 and 64 g/l, more specifically between 18 and 34 g/l.

Determination, Characterization and Quantification of the Sugars of the Active Ingredient The object is to determine the molar masses of carbohydrates present in the active ingredient. The results obtained by high-performance liquid chromatography are presented hereafter:

|  | Molar Mass MM (Da) | Degree of Polymerization | Level of Carbohydrates |
|---|---|---|---|
| Monosaccharides | MM ≤ 180 | DP 1 | 15% |
| Oligosaccharides & Polysaccharides | 180 < MM < 135 760 | 1 < DP < 754 | 85% |

The active ingredient for the most part consists of
Oligosaccharides of molar masses encompassed between 322 Da or a degree of polymerization of 2 and 1980 DA or a degree of polymerization of 11, and
Polysaccharides.

The level of each sugar is then determined by means of a standard range. The composition of simple sugars is summed up in the table below:

| Type of Sugar | Proportion (%) |
|---|---|
| Sucrose | 54.4 |
| Glucose | 33.3 |
| Fructose | 7.2 |
| Fucose | 5.0 |

The composition of simple sugars for the most part consists of oligosaccharides of sucrose and glucose.

An enzymatic hydrolysis of the active ingredient according to this invention is carried out with an α-amylase and makes it possible to release half of the amount of glucose obtained after acid hydrolysis. Therefore, a portion of the linked glucose, within the active ingredient, is in the form of α-glucans.

The glucidic fraction of the active ingredient according to this invention primarily consists of oligosaccharides of sucrose and glucose including a portion in the form of α-glucans, with a degree of polymerization of between 2 and 11.

Stability of the Active Ingredient pH Stability:

The pH stability study is carried out at 20° C. for a pH range varying from 2 to 10.

The active ingredient is stable at a concentration of 1 to 5%.

Temperature Stability:

The temperature stability study was carried out with the pH of the active ingredient for temperatures varying from 40 to 80° C. for 2 hours.

| Active Ingredient | T(° C.)/t (min) ||||||||| 
|---|---|---|---|---|---|---|---|---|---|
|  | 40° C. ||| 60° C. ||| 80° C. |||
|  | 30' | 60' | 120' | 30' | 60' | 120' | 30' | 60' | 120' |
| 1% | + | + | + | + | + | + | + | + | + |
| 2.5% | + | + | + | + | + | + | + | + | + |
| 5% | + | + | + | + | + | + | + | + | + |

The sign "+" relates to the stability of the product, and the sign "−" relates to its instability.

Ethanol Stability:

| Active Ingredient | Ethanol/Water (v/v) |||||||
|---|---|---|---|---|---|---|---|
|  | 10/90 | 20/80 | 30/70 | 40/60 | 50/50 | 60/40 | 70/30 |
| 1% | + | + | + | + | + | + | + |
| 2.5% | + | + | + | + | + | + | + |
| 5% | + | + | + | + | + | + | + |

The sign "+" relates to the stability of the product, and the sign "=" relates to its instability.

DMSO (Dimethyl Sulfoxide) Stability:

The DMSO stability study is carried out at 20° C. and at the pH of the active ingredient that is obtained.

| Active Ingredient | DMSO |
|---|---|
| 10% | + |
| 15% | + |
| 20% | − |

The sign "+" relates to the stability of the product, and the sign "−" relates to its instability.

Stability of Different Formulations

The active ingredient is introduced at a rate of 5% by weight in the following formulas:

Clear Gel:

| Carbopol Ultrez 10 | 0.5% |
|---|---|
| NaOH | Enough to produce pH = 6.3 |
| Glycerol | 10% |
| Polypropylene glycol | 10% |
| Preservative | 0.7% |
| Water | Enough to produce 100% |

Opaque Gel:

| Sepigel 305 | 3% |
|---|---|
| Lanol 99 | 25% |
| Preservative | Enough to produce 100% |

Emulsified Gel:

| Montanov 202 | 3% |
|---|---|
| Isopropyl myristate | 10% |
| Preservative | 0.7% |
| Lanol 1688 | 2% |
| Water | Enough to produce 100% |

Non-Ionic Emulsion:

| Montane 60 | 3% |
|---|---|
| Montanox 60 | 5% |
| Isopropyl palmitate | 20% |
| Preservative | 0.7% |
| Water | Enough to produce 100% |

Anionic Emulsion:

| Stearic acid | 7% |
|---|---|
| NaOH | Enough to produce pH = 7 |
| Isopropyl palmitate | 20% |

-continued

| | |
|---|---|
| Preservative | 0.7% |
| Water | Enough to produce 100% |

Cationic Emulsion:

| | |
|---|---|
| Amonyl DM | 5% |
| Cetearylic alcohol | 1% |
| Isopropyl myristate | 10% |
| Cetylic alcohol | 2% |
| PEG 100 stearate | 1% |
| Preservative | 0.7% |
| Water | Enough to produce 100% |

The results show an absence of precipitation of the active ingredient, and an absence of creaming or phase shift of the formula.

| Cosmetic Formulas | Stability |
|---|---|
| Aqueous Solution | ++ |
| Clear Gel | ++ |
| Opaque Gel | ++ |
| Emulsified Gel | ++ |
| Anionic Emulsion | ++ |
| Cationic Emulsion | ++ |

The reference "++" means stability, "+" means stability with a slight fluidification of the formula relative to the placebo, and "−" means instability.

Identification of the Active Fraction of the Active Ingredient

The following fractions of the active ingredient are identified:

Fraction A: The fraction of the ash obtained from incineration at 550° C. is taken up in distilled water. The solution is filtered, and its analysis shows that it contains 67% of the ash from the active ingredient.

Fraction B: The neutral carbohydrates of the active ingredient are purified by successive adsorption of the cationic compounds and then anionic compounds on ionic resins. The fraction is purified and comprises 87% sugars and a very small amount of proteins of between 1 and 10% and less than 2% of polyphenols.

Fraction C: The active ingredient is subjected to an acid hydrolysis, and then the solution is neutralized, freeze-dried, and then taken up in distilled water. This fraction C contains all of the compounds of the active ingredient, the sugars being in free form because of the conditions of acid hydrolysis.

To determine the active fraction or fractions, the capacity of the active ingredient is determined according to this invention to limit the production of interleukins-8 by reticular human fibroblasts subjected to UV radiation.

This study is carried out using an Elisa IL-8 metering.

| | Level IL-8 (fg/µg of Proteins) | Level of IL-8/ Attacked Control (%) |
|---|---|---|
| Non-Attacked Fibroblasts | | |
| Control | 565 | |
| Attacked Fibroblasts | | |
| Control | 1,304 | |
| 0.5% Active Ingredient | 845 | −35 |
| 0.5% Fraction A | 1,376 | 0 |

| | Level IL-8 (fg/µg of Proteins) | Level of IL-8/ Attacked Control (%) |
|---|---|---|
| 0.5% Fraction B | 942 | −28 |
| 0.5% Fraction C | 1,334 | 0 |

It is noted that fractions A and C are ineffective, while fraction B makes it possible to reduce the production of interkeukins-8 by the fibroblasts and therefore to limit the inflammation phenomenon.

It is therefore the oligosaccharides that impart their effectiveness to the active ingredient obtained from peony roots.

Cosmetic Formulations Including the Active Ingredient

These are possible embodiments of compositions, provided by way of illustration.

Cream:

| | | |
|---|---|---|
| A. | Water | Enough to produce 100% |
| | Butylene Glycol | 5% |
| | Carbopol Ultrez 20 | 1.5% |
| B. | DUB PGPR (Stéarinerie Dubois) | 5.00% |
| | DUB Vinyl (Stéarinerie Dubois) | 6.00% |
| | DUB MCT 5545 (Stéarinerie Dubois) | 5.00% |
| C. | DC 2503 (Dow Corning) | 3.00% |
| | Preservative | 0.70% |
| | Active Ingredient | 2.00% |
| D. | TiO$_2$ | 1.00% |
| | Sépifeel One (Seppic) | 1.00% |
| | CI 77492 (Sensient) | 1.00% |
| | CI 77491 (Hytech Laboratories) | 0.16% |
| | CI 77492 (Sienna Clays) | 0.02% |
| E. | NaOH | Enough to produce pH = 4.5 |

The production process consists in:

Mixing the composition A, heating it in a water bath at 80° C., while stifling mechanically at 1,000 rpm, thoroughly dispersing the gel.

Mixing B, heating it in a water bath at 80° C., while stifling magnetically.

Emulsifying B in A, with a rotor-stator at 1,700 rpm.

Keeping it at 40° C. and adding C in the order indicated above, with a rotor-stator at 1,800 rpm.

Mixing D with a mortar to thoroughly homogenize the powdered phase.

Keeping it at 30° C., mixing D, with a good dispersion of pigments.

Stirring with a rotor-stator at 1,000 rpm for good homogenization.

Adjustment of the pH with E and cooling while being stirred.

A thick, creamy, rose-orange emulsified gel is obtained. The spreading is soft, dry and very soft finish, light coverage, good appearance effect, good pigment hold.

Bio Sublimating Cream:

| | | |
|---|---|---|
| A. | Water | Enough to produce 100% |
| | Sucrose Ester 15P | 1.00% |
| B. | Shea Butter (Hytech Laboratory) | 10.00% |
| | Sal Butter (Hytech Laboratory) | 2.20% |
| | Cupuacu Butter (Hytech Laboratory) | 2.00% |
| | Cocoa Butter (Hytech Laboratory) | 2.00% |
| | DUB Wax A (Stéarinerie Dubois) | 5.50% |
| | DUB Aprilose (Stéarinerie Dubois) | 5.00% |
| C. | Active Ingredient | 2.00% |
| | Preservative | 0.7% |

The production process consists in the series of the following stages:

Mixing A, heating it in a water bath at 80° C., while stifling magnetically.

Mixing B, heating it in a water bath at 80° C., while stifling magnetically.

Emulsifying B in A with a rotor-stator at 2,500 rpm.

Keeping it at 55° C., adding C, in the order indicated above with a rotor-stator at 3,000 rpm.

Cooling while being stirred until homogenization is completed.

A thick beige emulsion with a chocolate/caramel odor is obtained.

The spreading is comfortable, slightly film-forming fatty finish, non-sticky.

In Vitro Tests

The object is to model the impact of pro-inflammatory mediators produced by fibroblasts when they are subjected to UV radiation, and doing so on adipocyte physiology.

For this purpose, the secretome of attacked fibroblasts is characterized, and the capacity of normal human pre-adipocytes to be differentiated when they are subjected to these pro-inflammatory mediators is studied.

Characterization of the Secretome:

Human fibroblasts are inoculated on plates, put in a suitable medium and under a suitable atmosphere, for an incubation at 37° C. for 3 days.

These fibroblasts are then subjected to UV radiation by a solar simulator, with energy of approximately 15 J/cm$^2$, and doing so for several days.

The supernatant is then recovered to determine the inflammatory profile and the impact of this secretome on the adipocyte physiology.

To characterize the inflammatory component of the secretome, protein arrays are used.

The profile of the pro-inflammatory mediators is modified: 30 factors are regulated, including 17 significantly relative to the non-attacked fibroblasts.

15 factors are over-regulated, such as:

Cytokines, interleukins, in particular IL-8, GRO, GROα that are responsible for the inhibition of the adipocyte differentiation, Growth factors, in particular VEGF involved in the response to stress and HFG that is responsible for the activation of the adipocyte differentiation, Receptors, in particular IL-6R or uPAR, responsible for the inhibition or the activation of the adipocyte differentiation.

2 factors are under-regulated, such as, for example:

The TIMP-1 involved in the response to stress.

To evaluate the impact of this secretome on the adipocyte physiology, the differentiation of the adipocytes by measurement of the accumulation of lipidic droplets that are characteristic of the pre-adipocytes in the course of differentiation is evaluated, and doing so in response to the treatment by the secretome of the fibroblasts obtained above.

The Oil Red O coloring is used.

Human pre-adipocytes are put in the culture medium, and then the culture medium is eliminated in favor of a medium promoting the adipocyte differentiation.

The medium is then replaced by the secretomes obtained from fibroblasts that are attacked or not by UV radiation.

The cells are fixed, rinsed, and colored with an Oil Red O solution.

The visualization of the lipidic droplets and their quantitative analysis is carried out by an image analysis system using a microscope.

The results are presented in the table below.

|  | Lipidic Droplets ($\times 10^4$ UA) | Adipocyte Differentiation (%) |
| --- | --- | --- |
| Secretome of Fibroblasts (Non-Attacked) | 2,407 |  |
| Secretome of Fibroblasts (Attacked) | 1,547 | −36% |

It is noted that the human fibroblasts produce an inflammatory secretome when they are subjected to solar irradiations.

This inflammatory secretome exerts deleterious effects on the physiology of the adipocytes by significantly reducing the adipocyte differentiation and the accumulation of lipidic droplets.

Effects of the Active Ingredient According to the Invention Obtained from Roots of the Peony Paeonia albiflora on the Inflammatory Profile:

The operating procedure is identical to the preceding one, but the pre-adipocytes are placed in secretome media obtained from attacked or non-attacked fibroblasts, this time in the presence or not of the active ingredient according to this invention at a rate of 0.5%.

The objective is to evaluate the capacity of the active ingredient according to the invention to limit the harmful pro-inflammatory exchanges between the reticular dermis and the hypodermis. For this purpose, the effects are analyzed using protein arrays.

The results are expressed for fibroblasts that are attacked and treated with the active ingredient versus fibroblasts that are attacked and not treated. The effects on the proteins relative to the adipocyte differentiation and the response to stress are found there.

| Protein Profile (%) |  |
| --- | --- |
| Adipocyte Differentiation Inhibitors |  |
| FAs/TNFRSF6 | −11 |
| GRO | −17 |
| GRO-α | −33 |
| IL-6R | −31 |
| IL-8 | −39 |
| Activators |  |
| HGF | +47 |
| uPAR | +41 |
| Response to Stress |  |
| TIM-1 | +26 |
| TIMP-2 | +13 |
| VEGF | +41 |

It is also possible to use an ELISA IL-8 metering to determine the effects of the active ingredient according to this invention on the release of the IL-8 by fibroblasts after activation of the inflammation.

The results are presented in the table below.

|  | Level of IL-8 (fg/µg of Proteins) | Level of IL-8 Control (%) |
|---|---|---|
| Non-Attacked Fibroblasts | | |
| Control | 640 | |
| 0.50% Active Ingredient | 642 | |
| Attacked Fibroblasts | | |
| Control | 1,437 | |
| 0.25% Active Ingredient | 1,022 | −29 |
| 0.50% Active Ingredient | 808 | −44 |

It is noted that the active ingredient based on roots of the peony Paeonia albiflora according to this invention makes it possible to reduce significantly the synthesis of cytokines or receptors such as Fas/TNFRSF6, GRO, GRO-α, IL-6 and IL-8, limiting the inflammation phenomenon and thus promoting the adipocyte differentiation.

In addition, the active ingredient based on roots of the peony Paeonia albiflora according to this invention makes it possible to protect the fibroblasts from the stress induced by UV radiation by increasing the synthesis of TIMP-1 and TIMP-2 and VEGF.

The test on the release of IL-8 by the fibroblasts after activation of inflammation was also performed on two other extracts containing oligosaccharides of D-glucose, to conduct a comparative test, and to demonstrate that the origin of the oligosaccharides is important:

(1) one extract of betony (Stachys officinalis), containing a major presence (71%) of free sugars, preferably of fructose, and oligosaccharides (29%) of glucose and galactose having a DP between 2 and 10, and (2) one extract from rye (Secale cereale), whose content is 40% of free carbohydrates, and 60% of oligosaccharides of glucose and xylose having a mean DP of less than 5.

The results obtained with these two extracts do not respond positively to the test, unlike the hydrolyzate according to the invention.

Effects of the Active Ingredient According to the Invention Obtained from Roots of the Peony Paeonia albiflora on the Adipocyte Physiology:

Study of the Direct Impact

|  | Lipidic Droplets ($10^4$ UA) | Adipocyte Differentiation (%) |
|---|---|---|
| Control | 2,587 | 100 |
| 0.50% Active Ingredient | 1,752 | 74 |

Tested at 0.5%, the active ingredient obtained from the root of the peony Paeonia albiflora does not have a direct effect on the adipocyte differentiation.

Study of the Impact via the Secretome

|  | Lipidic Droplets ($10^4$ UA) | Adipocyte Differentiation (%) |
|---|---|---|
| Secretome of Non-Attacked Fibroblasts | | |
| Control | 2,407 | |
| 0.50% Active Ingredient | 2,431 | |
| Secretome of Attacked Fibroblasts | | |
| Control | 1,547 | |
| 0.25% Active Ingredient | 2,272 | +47 |
| 0.50% Active Ingredient | 2,420 | +56 |

The treatment of the pre-adipocytes by the secretome of attacked fibroblasts leads to a significant reduction of their differentiation. It is noted that the active ingredient obtained from roots of the peony Paeonia albiflora preserves the capacity for adipogenesis of the pre-adipocytes.

In Vivo Tests

Conditions of the Tests:

The tests are conducted with the active ingredient according to the invention, in emulsion at 2%, obtained from roots of the peony Paeonia albiflora.

The emulsion formulation that is adopted is the following:

| | |
|---|---|
| Isonyl Isononoate (DUB ININ, Stéarinerie Dubois) | 5.0% |
| Cetearylic Alcohol/Cetearylic Glucosides (Montanov 68 Seppic) | 5.0% |
| Active Ingredient | 2.0% |
| Isopropyl Myristate (IPM) | 2.0% |
| Preservatives | 0.7% |
| Water | Enough to produce 100% |

The tests are carried out on a panel, in comparison with a placebo, at a rate of two daily topical applications, morning and evening, for 42 consecutive days.

The cutaneous characteristics that are studied are:

Thickness of the adipose tissue

Volumes of the face

Biomechanical properties of the skin

Cutaneous relief

The panel that is adopted consists of individuals having a mean age of greater than 45 years, having skin that has been exposed to light, and having a more hollow face and vertical wrinkles on the cheeks, a sign of the loosening of the skin and modification of volumes.

Two groups have thus been determined:

Group A: 19 volunteers aged 46 to 70 years, mean age 60±6 years having applied the placebo on the entire face.

Group B: 19 volunteers aged 44 to 69 years, mean age 62±6 years, having applied the active ingredient according to this invention on the entire face.

Study of the Adipose Volume:

A study area is defined and referenced very specifically for each patient so as to make possible a superposition. This area is located essentially at the same location for all of the subjects, at the bottom of the face.

The acquisition of information is done using an echograph.

The results show an increase of +9.8% of the thickness of the adipose tissue, with a significance index p=0.0480, therefore making it possible to adopt this value.

In addition, this increase is present in 68% of the volunteers having received the application of the active ingredient according to the invention.

The areas of the face that become hollow can thus be filled in.

Study of the Volumes of the Face:

The purpose of the acquisitions is the volume of the bottom of the face. The measurement is taken by a fringe projection device, dedicated to measurements of the important changes in volume of the face and the body.

An area of interest of 40×40 mm on the cheek is cut out during the 3D digital acquisition.

The upper positive volume on the surface of the skin makes it possible to conclude that there is or is not a redensifying effect.

The results show a variation relative to the placebo of +18.5% on the hollow volumes of the cheek with a significance index p=0.0049, making it possible to adopt this result.

In addition, 84% of the volunteers who have received the active ingredient show an increase of the positive volume in the hollows of the cheeks.

Study of the Mechanical Properties of the Skin:

This study is carried out using a Cutometer® on the cheeks.

The skin is sucked into the opening of a probe by a constant vacuum and a constant duration.

Several successive intakes are conducted, and the penetration of the skin in the opening is measured by optical means.

In this study, the following are adopted as calculated parameters:

(i) Elasticity
(ii) Tone.

The results are as follows:

|  | Variation/Placebo (%) |
| --- | --- |
| Elasticity | +12.4% (p = 0.0244) |
| Tone | +8.1 (p = 0.0405) |

In addition, it is noted that:
(i) The effect of improvement of the elasticity of the skin is observed in 79% of the volunteers.
(ii) The effect of improvement of the tone of the skin is observed in 68% of the volunteers.

5/Study of the Effects on the Cutaneous Relief

The study is conducted using a fringe-spraying device that makes it possible to measure the cutaneous relief and to derive the following roughness parameters:

Sq: Root mean square of surface roughness
Sa: Arithmetic mean of surface roughness A reduction of these parameters is characteristic of an improvement of the relief of the surface studied.

The results that are obtained are indicated in the following table

|  | Variation/Placebo (%) |
| --- | --- |
| Parameter Sa | −11.9% (p = 0.0438) |
| Parameter Sq | −12.1% (p = 0.0308) |

The study shows that:

The parameter Sa was reduced in 68% of the subjects treated with the active ingredient according to the invention, and The parameter Sq was reduced in 74% of the subjects treated with the active ingredient according to the invention.

The active ingredient obtained from roots of *Paeonia albiflora* contributes to minimizing the marks of ageing that are the vertical furrows that form on the cheeks with age and exposure to sun.

Subjective Evaluation

The evaluation is carried out by analysis of self-evaluation questionnaires of the volunteers who have tested the products.

|  | Total of the Responses "Agree Somewhat" and "Agree" (%) | | |
| --- | --- | --- | --- |
|  | Placebo Group | Active Ingredient Group | p |
| The oval of my face seems to be redrawn | 72% | 89% | 0.0981 |
| My face has increased in volume | 67% | 88% | 0.0562 |
| My face looks younger | 61% | 83% | 0.0622 |
| My large and small wrinkles are less visible | 67% | 100% | 0.0013 |
| This emulsion causes a plumping-up effect | 72 | 94% | 0.0305 |

Thus, 94% of the volunteers believe that the active ingredient based on roots of the peony *Paeonia albiflora* according to the invention, formulated in an emulsion, has a plumping-up effect and improves the design of the contours of the face.

The invention claimed is:

1. A method of providing a plumping-up effect to skin, comprising topically applying to skin of a subject in need thereof a cosmetic composition comprising an effective amount of a cosmetic active ingredient comprising an enzymatic hydrolyzate of roots of *Paeonia albiflora* with at least 30% of carbohydrates by weight relative to the total weight of dry materials of active ingredient,
    wherein the 30% of carbohydrates comprises at least 80% oligosaccharides,
    wherein the oligosaccharides are at least in part oligosaccharides of sucrose and glucose,
    wherein there is more sucrose than glucose,
    wherein the active ingredient is obtained by at least the following process:
        solubilization of powder from *Paeonia albiflora* roots in water;
        enzymatic hydrolysis;
        separation of soluble and insoluble phases; and
        enzymatic deactivation by heat treatment.

2. The method of providing a plumping-up effect to skin according to claim 1, wherein the cosmetic composition is topically applied at least once daily.

3. The method of providing a plumping-up effect to skin according to claim 1, wherein the cosmetic active ingredient is between 0.1 and 10% by total weight of the cosmetic composition.

4. A method for increasing thickness and volume of adipose tissue, comprising topically applying to skin of a subject in need thereof a cosmetic composition comprising an effective amount of a cosmetic active ingredient comprising an enzymatic hydrolyzate of roots of *Paeonia albiflora* with at least 30% of carbohydrates by weight relative to the total weight of dry materials of active ingredient,
    wherein the 30% of carbohydrates comprises at least 80% oligosaccharides,
    wherein the oligosaccharides are at least in part oligosaccharides of sucrose and glucose,
    wherein there is more sucrose than glucose,
    wherein the active ingredient is obtained by at least the following process:
        solubilization of powder from *Paeonia albiflora* roots in water;

enzymatic hydrolysis;
separation of soluble and insoluble phases; and
enzymatic deactivation by heat treatment.

5. The method for increasing thickness and volume of adipose tissue according to claim 4, wherein the cosmetic composition is topically applied at least once daily.

6. The method for increasing thickness and volume of adipose tissue according to claim 4, wherein the cosmetic active ingredient is between 0.1 and 10% by total weight of the cosmetic composition.

7. A method for controlling communication between dermis and hypodermis, comprising topically applying to skin of a subject in need thereof a cosmetic composition comprising an effective amount of a cosmetic active ingredient comprising an enzymatic hydrolyzate of roots of *Paeonia albiflora* with at least 30% of carbohydrates by weight relative to the total weight of dry materials of active ingredient,
  wherein the 30% of carbohydrates comprises at least 80% oligosaccharides,
  wherein the oligosaccharides are at least in part oligosaccharides of sucrose and glucose,
  wherein there is more sucrose than glucose,
  wherein the active ingredient is obtained by at least the following process:
    solubilization of powder from *Paeonia albiflora* roots in water;
    enzymatic hydrolysis;
    separation of soluble and insoluble phases; and
    enzymatic deactivation by heat treatment.

8. The method for controlling communication between dermis and hypodermis according to claim 7, wherein the cosmetic composition is topically applied at least once daily.

9. The method for controlling communication between dermis and hypodermis according to claim 7, wherein the cosmetic active ingredient is between 0.1 and 10% by total weight of the cosmetic composition.

10. A method for filling in loss of structure and correcting for loosening of skin, comprising topically applying to skin of a subject in need thereof a cosmetic composition comprising an effective amount of a cosmetic active ingredient comprising an enzymatic hydrolyzate of roots of *Paeonia albiflora* with at least 30% of carbohydrates by weight relative to the total weight of dry materials of active ingredient,
  wherein the 30% of carbohydrates comprises at least 80% oligosaccharides,
  wherein the oligosaccharides are at least in part oligosaccharides of sucrose and glucose,
  wherein there is more sucrose than glucose,
  wherein the active ingredient is obtained by at least the following process:
    solubilization of powder from *Paeonia albiflora* roots in water;
    enzymatic hydrolysis;
    separation of soluble and insoluble phases; and
    enzymatic deactivation by heat treatment.

11. The method for filling in loss of structure and correcting for loosening of skin according to claim 10, wherein the cosmetic composition is topically applied at least once daily.

12. The method for filling in loss of structure and correcting for loosening of skin according to claim 10, wherein the cosmetic active ingredient is between 0.1 and 10% by total weight of the cosmetic composition.

* * * * *